United States Patent

El Bounia et al.

[11] Patent Number: 5,448,908
[45] Date of Patent: Sep. 12, 1995

[54] DEVICE FOR THE MEASUREMENT OF VISCOELASTICITY OF PRODUCTS, AND PARTICULARLY THOSE WITH LOW VISCOSITY

[75] Inventors: Nour-Eddine El Bounia, Artrix; Cathy Rey, Tilh, both of France

[73] Assignee: Societe Nationale Elf Aquitaine, France

[21] Appl. No.: 204,153
[22] PCT Filed: Aug. 28, 1992
[86] PCT No.: PCT/FR92/00829
§ 371 Date: Mar. 2, 1994
§ 102(e) Date: Mar. 2, 1994
[87] PCT Pub. No.: WO93/05383
PCT Pub. Date: Mar. 18, 1993

[30] Foreign Application Priority Data

Sep. 2, 1991 [FR] France ............... 91 10828

[51] Int. Cl.6 .................................. G01N 11/14
[52] U.S. Cl. .................................... 73/54.35
[58] Field of Search ............... 73/54.28, 54.39, 54.31, 73/54.32, 54.33, 54.34, 54.35

[56] References Cited

U.S. PATENT DOCUMENTS

| | | | |
|---|---|---|---|
| 2,096,222 | 10/1937 | Bock | 73/54.35 |
| 2,828,621 | 4/1958 | Rosenberg | 73/54.32 |
| 3,350,922 | 11/1967 | Kim et al. | 73/54.28 |
| 4,214,475 | 7/1980 | Carter et al. | 73/54.32 |

Primary Examiner—Hezron E. Williams
Assistant Examiner—Michael J. Brock
Attorney, Agent, or Firm—Ostrolenk, Faber, Gerb & Soffen

[57] ABSTRACT

Device for the measurement of viscoelasticity of products, and in particular those with low viscosity. It is of a type including a male cupel equipped with a cylindrical separating partition which can be introduced into an annular chamber arranged in a body of a female cupel and receiving the product to be measured, and a drive mechanism for movement around an axis of rotation of one of the cupels in relation to the other, and characterized in that it has, in addition, the means to close in an impervious manner the annular chamber.

15 Claims, 1 Drawing Sheet

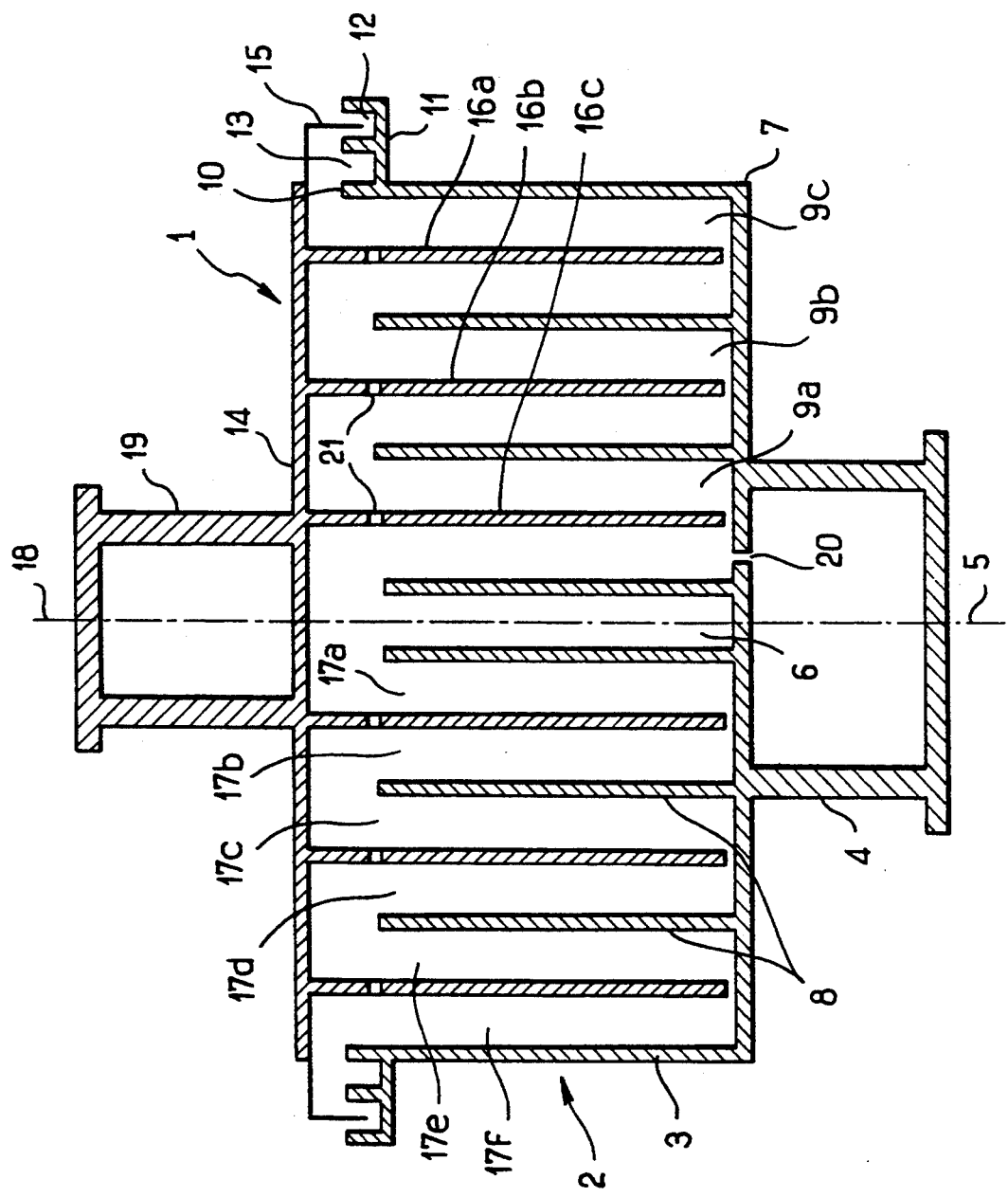

DEVICE FOR THE MEASUREMENT OF VISCOELASTICITY OF PRODUCTS, AND PARTICULARLY THOSE WITH LOW VISCOSITY

BACKGROUND OF THE INVENTION

1. Field of the Invention

This invention concerns a device for the measurement of the viscoelasticity of products, and particularly those with a low viscosity.

2. Description of the Related Art

It is often necessary when measuring the physico-chemical characteristics of a given product, such as a resin, a paint or a plastic, to measure and know the viscoelasticity of the product in question.

A great many devices for measuring viscoelasticity have been proposed. Some consist of two flat plates between which the product to be measured is deposited. An angular movement of one plate in relation to the other creates a shear torque in the product. A measurement of this shear torque serves to determine the viscoelasticity of the product deposited between the plates.

Other devices known under the generic designation of Couette type rheometers have a female cupel into which is put a male cupel, the cupels being cylindrical and the product to be measured being deposited in the female cupel. The product is sheared between the cupels, one of which is fixed and the other mobile.

The theory of rheometers of the Couette type and their structure are described in "Initiation á la Rheologie" (Introduction to Rheology), 1983 edition of "Technique et Documentation" (Lavoisier).

Other devices for measuring the viscoelasticity or rheometers are disclosed in FR-A-2,531,538, U.S. Pat. Nos. 3,667,286 and 2,828,621.

A serious drawback of all rheometers used until now resides in the fact that they operate in the open air. Because of this, when the measuring device is put into a heating cabinet or an oil bath to raise the product or substance to be measured to a designated temperature, which depends, among others, on the nature of the product to be measured, it follows that, in products containing a solvent, the solvent evaporates in more or less large quantities, and this occurs no matter how fast the product is put into the female cupel, or into the heating cabinet or oil bath. However, the evaporation of the solvent leads at least to a change in the physical characteristics of the product. Consequently, the shear torque is affected and this often leads to erroneous results.

Another serious drawback is related to the very structure of known cylindrical rheometers. Such rheometers, in addition to the fact that they are open and thus likely to permit evaporation of solvent, are relatively large in size and necessitate a change of the shear torque measuring sensor whenever there is a change to another product with a different viscosity. This results in an increased risk of damage to sensors which, furthermore, are very expensive. In addition, they are poorly suited to an alternating or sinusoidal movement between the mobile and fixed cupels due to the inevitable inertia caused by the oversizing of the cupels.

SUMMARY OF THE INVENTION

The purpose of this invention is to palliate the above-mentioned disadvantages and to propose a measuring device which is impervious to the ambient atmosphere, of small size and adaptable to presently-used viscoelasticity meters.

An advantage of this invention resides in the fact that the device operates in an impervious medium, without any evaporation of solvent.

Another important characteristic is that several annular chambers are arranged in the female cupel, for the measurement of the viscoelasticity of products with a very low viscosity.

In addition, the device under this invention is provided with means for the direct introduction of products into the female cupel, which prevents any evaporation of solvent when the product to be measured is put into the female cupel.

Other advantages and characteristics are to be understood more clearly on reading the description of a preferred design of the invention, as well as the appended drawing.

BRIEF DESCRIPTION OF THE DRAWING

The only FIGURE is a sectional view of the measuring device according to a preferred embodiment of the present invention.

DESCRIPTION OF THE PREFERRED EMBODIMENT

The device under the invention includes a male cupel (1), and a female cupel (2) consisting of a cylindrical body (3). The female cupel (2) can be driven in continuous rotation or be given an alternating rotary movement of given frequency, or even be moved vertically in relation to the male cupel (1). The rotary drive mechanism can be of any appropriate type, such as, for example, a motor, not shown, integral with a drive piece (4) which turns around an axis of rotation (5). The mobile female cupel (2), in comparison to the fixed male cupel (1), has a central hollow hub (6) which is closed at its bottom by the bottom (7) of the body (3) and open at its top. Arranged concentrically, and all around a central hub (6), there are cylindrical walls, for example two in number, which delimit between them three annular chambers (9a, 9b, 9c). Preferably, the height of the walls (8) is greater than the height of the product to be measured which is introduced in chambers (9), as described below. The thickness (2) of the walls (8) is constant, for example equal to 1 mm.

At the top of the body (3) and slightly below the free edge (10) of the body, there is a rim (11) in which there is a first cylindrical groove (12) filled with oil and a second cylindrical groove (13) filled with solvent.

The male cupel (1) includes a closure wall (14) which has a peripheral skirt (15), the free edge of which is immersed in the oil of the first groove (12), without being in contact with the bottom of the groove (12). The closure wall (14), the skirt (15) and the groove (12) filled with oil, taken together, constitute an impervious system which prevents any evaporation to the outside of the solvent contained in the product to be measured and filling at least partially the annular chambers (9a, 9b, 9c).

Separating partitions, for example three in number, and designated by 16a, 16b and 16c, are integral with the closure wall (14), and are cylindrical and concentric. The partitions (16a, 16b, 16c) are arranged inside the annular chambers (9a, 9b 9c) in such a way that each partition delimits to the inside of the corresponding chamber two narrow spaces. In the depicted example, this gives six narrow spaces (17a to 17f), whose thickness is selected in such a way that the shear gradient be constant from one space to another. This is obtained by selecting the internal radii of the annular chambers (9a, 9b, 9c) so that the two inner radii (Rn/Rn−1)+t=S and ≦1.15 for the case of narrow spaces where t is the thickness of each wall.

Partitions 16a to 16c have a height such that their lower edge does not come into contact with the bottom wall of the body (3).

Using any appropriate means, such as a syringe, the product to be measured is put into the female cupel (2) through an opening (20) in the wall of the bottom (7). The syringe is kept in place during measurement so as to maintain the imperviousness of the device. Each partition (16a to 16c) has one or more openings (21) at the top and, in every case, above the level of the product, to permit a balancing of pressures inside the device, on the one hand, and the passage of the product from one chamber to another, any overflow being collected in the central core (6), on the other.

An appropriate sensor for the measurement of shear torque is mounted on a shaft (18) of a piece (19) integral with the closure wall (14).

In the depicted example, the thickness t of each wall of the central hub, of the annular chambers and of the separating partitions of the narrow spaces is constant and equal to 1 mm. The radius R1 of the central hub is counted from axis (5) which is aligned with axis (18), up to the outer face of the wall of the central hub (6). The internal radius R2 corresponding to the first space delimited by the wall of the central hub and the opposing or internal face of the adjacent separating partition (16c) is also counted from axis (5). The other radii R3 to R7 are counted as described above. A ratio R2/R1=1.07 is taken, since studies and experiments have demonstrated that excellent results are obtained with such a ratio value. It results that R3=(R2+t)×1.07; progressively, the value of the other radii are calculated. In every case, it is necessary that $$\frac{R2 - R1}{R1} \leq 0.15$$

to be able to consider, in the case of a narrow space, the shear stress as constant. And in fact, the product in each space is subjected to a shear gradient γ. As γ only depends on shear stress, it is thus also held constant, on the condition that a given geometry be respected. If ω designates the speed of rotation, we have, for a traditional Couette geometry:

$$\alpha = \frac{\omega R1}{R2 - R1}$$

where R1 and R2 are respectively the internal and external radii of the space. When considering narrow spaces, as is the case under this invention, and by requiring that the shear gradient be constant in all spaces, the value of the radii R1 to R7 mentioned above are determined. With R1=10 mm, R2/R1=1.07 and t=1 mm, this gives the following: R2=10.7 mm; R3=12.52 mm up to R7=21.16 mm.

It has been possible to demonstrate by calculation and experiments carried out with the software program equipping the Rheometrics RDS 7700 II, of the firm of Rheometrics, that the sensitivity of the device under this invention is increased by a factor of at least 13 in comparison to devices used earlier in the field. To be sure, sensitivity can still be increased even more, by increasing the number of spaces, the characteristics of which were described above.

With the device covered under this invention, it is also possible to measure the modulus of elasticity G' and modulus of viscosity G" as well as the complex viscosity η* of any product whatsoever, even with a low viscosity.

The small size of the device under this invention as well as the nature of the materials with which it can be made make it even more attractive, since it can be easily made by machining if it is in metal or by injection if it is made of plastic. In this latter case, it can be of the disposable type, as its cost would be reduced to a great extent, compared to the cost of devices used earlier in the field.

The device operates as follows: The device is put into an oven, not depicted, the temperature of which is raised to a certain value which depends on the product to be measured. Once the device is raised to a certain temperature, a preset quantity of the product to be measured is introduced through the inlet opening (20). As soon as the product is evenly distributed in the spaces (17a to 17f) by way of the passages arranged between the free edges of the separating partitions (16a to 16c), the communicating opening (21) and, possibly, the overflow flowing inside the central hub (6), the female cupel (2) is driven in continuous or alternating rotation, according to the selected procedure. The relative movement between the male (1) and female (2) cupels introduces into each space a shear torque which is measured by the measuring sensor. The total measured shear torque (Tt) is calculated with the formula:

$$Tt = \sum_i Ti$$

where $$i = 1 \text{ to } 6$$

with $$Ti = \frac{\tau \cdot 4\pi h \cdot (Ri + t)_2 \cdot R_{2i} + 1}{(Ri + t)_2 + R_{2i} + 1}$$

"i" being an integer and between 1 and 6 for the case in question, h being the height of the product in the female cupel and τ being the average shear stress. These formulas apply in the case of continuous shear.

It is to be noted that the closure and sealing system of the device prevent any evaporation to the outside of solvent contained in the product to be measured.

The groove full of solvent is of great interest when injecting the product into a closed space so as to create, before injection of the product, an atmosphere saturated with solvent at the measuring temperature, thus preventing the evaporation of the solvent contained in the product to be measured.

On the assumption that direct injection into female cupel (2) would not be used, the product is deposited cold in the female cupel (2). Once the test specimen is in place, the whole is raised to a preset measuring temperature. In this case as well, the solvent of the second groove (13) brings about very quickly an atmosphere saturated with solvent.

To be sure, the invention is not at all limited to the method of the described and depicted example. It is readily subject to numerous variations accessible to specialists, depending upon the planned applications and without departing for this reason from the context of the invention.

We claim:

1. A measuring device comprising: a male cupel having a closure wall including a peripheral skirt, and a cylindrical separating partition attached to the closure wall;
   a female cupel having a body, the body including an annular chamber for receiving the separating partition and an external annular rim having a first groove for receiving the peripheral skirt, the female cupel being provided for receiving a product to be measured;
   a drive mechanism for movement around an axis of rotation of one of the cupels in relation to the other; and
   means for closing, in a manner impervious to an ambient atmosphere, the annular chamber.

2. The device of claim 1, wherein the first groove is filled with oil.

3. The device of claim 2, further comprising a second grove arranged in the annular rim between the body of the female cupel and the first groove.

4. The device of claim 3, wherein the second groove is filled with a solvent.

5. The device of claim 3, wherein the first and second grooves are circular and concentric.

6. The device of claim 1, wherein: the body of the female cupel includes at least three concentric annular chambers around a central hollow hub; and the male cupel includes separating partitions integral therewith and adapted to be received by the annular chambers.

7. The device of claim 6, wherein each of the separating partitions is equipped with at least one opening arranged above the level of the product to be received in the female cupel.

8. The device of claim 6, wherein the radius of the annular chambers increases from the hub towards the exterior.

9. The device of claim 6, wherein the central hub is hollow and open at its top.

10. The device of claim 6, wherein the separating partitions of the male cupel and cylindrical walls of the annular chamber of the female cupel serve together to delimit narrow spaces.

11. The device of claim 10, wherein the radius of the spaces increases from the axis of rotation towards the outside.

12. The device of claim 11, wherein the radii of the spaces are between 10 mm for the smallest to 21.16 mm for the largest.

13. The device of claim 1, wherein the female cupel is provided with an inlet for the introduction of the product to be measured.

14. The device of claim 13, wherein the inlet of the product is an opening arranged in the bottom of one of the annular chambers.

15. The device of claim 1, wherein the female cupel is adapted to be driven in an alternating rotary movement in relation to the male cupel.

* * * * *